(12) United States Patent
Folio

(10) Patent No.: US 9,541,822 B2
(45) Date of Patent: Jan. 10, 2017

(54) RADIOGRAPHIC MARKER THAT DISPLAYS AN ANGLE IN DEGREES ON PORTABLE X-RAYS

(75) Inventor: Les R. Folio, Alexandria, VA (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/005,024

(22) PCT Filed: Mar. 14, 2012

(86) PCT No.: PCT/US2012/029108
§ 371 (c)(1),
(2), (4) Date: Jan. 7, 2014

(87) PCT Pub. No.: WO2012/125750
PCT Pub. Date: Sep. 20, 2012

(65) Prior Publication Data
US 2014/0112454 A1 Apr. 24, 2014

Related U.S. Application Data

(60) Provisional application No. 61/452,364, filed on Mar. 14, 2011.

(51) Int. Cl.
*G03B 42/04* (2006.01)
*A61B 6/04* (2006.01)
(Continued)

(52) U.S. Cl.
CPC .......... *G03B 42/047* (2013.01); *A61B 6/4283* (2013.01); *A61B 6/547* (2013.01); *A61B 90/39* (2016.02);
(Continued)

(58) Field of Classification Search
CPC .......... A61B 6/42; A61B 6/44; A61B 6/4283; A61B 6/4291; A61B 6/547; A61B 90/39; A61B 2090/069; A61B 2090/3966; G03B 42/04; G03B 42/042; G03B 42/045; G03B 42/047; G01C 9/00; G01C 9/10
(Continued)

(56) References Cited

U.S. PATENT DOCUMENTS 2,649,548 A * 8/1953 Greenberg ........... A61B 5/1071
378/165
4,058,733 A 11/1977 Stembel
(Continued)

FOREIGN PATENT DOCUMENTS

GB 2074730 A * 11/1981 ............... G01C 9/10

*Primary Examiner* — David E Smith
(74) *Attorney, Agent, or Firm* — Klarquist Sparkman, LLP

(57) ABSTRACT

The present invention provides methods/techniques and apparatus for displaying an angulation of a cassette and thus a patient at a time when an x-ray image is taken to provide for a better comparison of day to day improvement of the patient. More specifically, the present invention, allows a movable object to roll freely within in a passageway within an enclosure in relation to an angulation of a cassette. In order to correlate the position of the movable object in the enclosure with the angle at which the cassette is currently placed, a plurality of markers are disposed in or protruded from the inner surface of the passageway. Based upon the position of the movable object in relation to a particular marker at the time an x-ray is taken, the user can identify the angulation at which the cassette is currently positioned.

21 Claims, 13 Drawing Sheets

(51) Int. Cl.
*A61B 6/00* (2006.01)
*G01C 9/10* (2006.01)

(52) U.S. Cl.
CPC .............. *G01C 9/10* (2013.01); *G03B 42/04* (2013.01); *A61B 2090/069* (2016.02); *A61B 2090/3966* (2016.02)

(58) Field of Classification Search
USPC .............. 378/162–165, 177, 182, 204, 205
See application file for complete search history.

(56) References Cited

U.S. PATENT DOCUMENTS

| | | | | |
|---|---|---|---|---|
| 4,267,641 A | * | 5/1981 | Shinozaki | G01C 9/00 33/365 |
| 5,166,966 A | * | 11/1992 | Steinmeyer | 378/156 |
| 5,450,676 A | * | 9/1995 | Thornsberry | 33/366.16 |

* cited by examiner

30°

0°

RADIOGRAPHIC MARKER THAT DISPLAYS AN ANGLE IN DEGREES ON PORTABLE X-RAYS

RELATED APPLICATIONS

This application is a 35 U.S.C. §371 U.S. national entry of International Application PCT/US2012/029108 (WO 2012/125750) having an International filing date of Mar. 14, 2012, which claims the benefit of U.S. Provisional Application Ser. No. 61/452,364, filed Mar. 14, 2011, the teachings of which are incorporated herein by reference.

FIELD OF THE INVENTION

The present invention relates to a method and apparatus for displaying the angle of an object being x-rayed, on an x-ray image. More particularly, the disclosure relates to a method displaying the angulation at which an x-ray image was taken by a portable x-ray machine.

BACKGROUND OF INVENTION

The portable chest x-ray (CXR) is one of the most commonly requested diagnostic medical tests performed in hospitals throughout the world. Portable CXRs are performed nearly daily on some of the sickest patients in hospitals, including those with pleural effusions, support lines and tubes. Thus, patients who require CXRs the most, are in the intensive care unit of the hospital.

A portable CXR is obtained typically at a patient's hospital bed when the patient is too sick to travel to the radiology department for an optimal upright posterior-anterior (PA) and lateral CXR or upright abdomen. Upright images more effectively evaluate effusions, e.g., as fluid settles due to gravity. Conversely, any trapped air rises and when found together in the same cavity with fluid, (e.g., such as in hydropneumothorax, abscess or empyema), an air-fluid level (for example) can be detected. Air collections (i.e., collections of trapped air) alone can also be realized in erect projections. If one does not know the degree of upright projection, however, one cannot rule out the presence of air. Additionally, abdomen portable projections are often obtained in decubitus positions. In this position the patient is placed on their side to make use of gravity and perpendicular x-ray beams to demonstrate free air, or air fluid levels.

The portable CXR is usually not imaged at a fully upright position because the x-ray source would have to be placed nearly in the patients lap in order to achieve a fully upright position and thus obtain a similar erect orientation as would be obtained in a radiology department. Instead, most CXRs are obtained at 45 degrees or less, often due to patient condition, or a technologist style/training. Accordingly, many portable CXRs are obtained at 45 degrees or less (though the exact angle is unknown to the medical community, due to the lack of a device to measure such an angle), often due to the patient's condition, or the style or training of the technologist or technician operating the CXR.

For this reason, portable radiography, such as CXRs, has been well documented as often being inconsistent, inaccurate and inadequate due to the inability to consistently and repetitively place the patient at a specific angle in relation to gravity. As stated above, in order for a radiologist to achieve an optimal quality of interpretation, the technologist must attempt to position a patient in the most upright position. In reality, however, the patient's position must also be balanced with his or her condition and their ability to achieve this nearly upright position. Positioning the patient in the most upright position provides for the best evaluation of effusions, rules out the presence of free air, and/or allows for a more accurate detection of air-fluid levels. Optimally, the images are obtained at similar angles each day to allow for accurate comparisons between each consecutive day.

Unfortunately, there are many instances where clinicians will order a CT (Computed Tomography) to differentiate effusion from consolidation (infection such as pneumonia), or to simply compare effusions since upright angulation is rarely truly known due to complications in angulation consistency. Thus, the patient is exposed to about 100 times more radiation; hundreds of dollars of increased expenditures for the more expensive technology and dangerous patient transport to the radiology department.

FIGS. 7A, B illustrate a comparison of a patient in an upright position and in a nearly supine position (lying down) taken by CXRs on different days. This comparison shows the change in opacification (representing effusion) depending on cassette (and hence a patient) angle. FIG. 7A shows an upright CXR demonstrating a left pleural effusion. The up arrow, used in conventional x-ray images, indicates an upright projection to the radiologist. However, there is no rule as to how "upright" the patient is among technologists; rather, this is a subjective decision based on the technologists choice and how busy they are. Additionally, there is no current method to evaluate technologist performance. FIG. 7B is more supine and shows the effusion distributed as a hazy ill-defined opacity over the lower left hemithorax (i.e., the left side of the chest).

Not knowing the degree of angulation in which each CXR is taken makes objective comparison of the amount of effusion impossible in most cases. For example, the right hand image can falsely indicate improvement of effusion. However, the next day (not shown here) could demonstrate an image similar to FIG. 7B (i.e., showing no effusion). Conversely, the two exams could falsely represent changing consolidation rather than effusion itself, leading clinicians to believe there is a worsening infection. Of note, effusions often mask or mimic consolidations (x-ray indicators of pneumonia). Misunderstanding of physiological process of portable x-ray exams, enhanced by an unknown patient angulation; too often leads to unnecessary use of CT (higher radiation and cost), as noted above.

Additionally, effusions often indicate the severity of a patient's condition and at times require drainage. Accordingly, increasing effusion over time is one indicator of the need for immediate thoracentesis (drainage of developing effusion). Thus, accurately quantifying or identifying the presence of an effusion, through use of an angulation measurement is highly necessary and at times a matter of life or death.

As also can be seen by FIGS. 7A, B there are currently no adequate quantitative markers on conventional x-ray images that indicate the degree/angle at which the x-ray image was taken. That is, conventional x-ray images only differentiate between supine and non-supine positions (i.e., upright and lying down).

Thus, there is a need for a device and method for more accurately quantifying the angulation at which an x-ray, for example, a CXR is taken. It would be particularly desirable to provide such a device and method that would allow the radiologist or providing physician to determine the degree of angulation by a glance as well as having left and right markers for every x-ray. Such devices preferably would be simple in construction and less costly than prior art devices.

BRIEF SUMMARY OF THE INVENTION

The present invention provides methods/technique and apparatus for displaying an angulation of a patient and the x-ray cassette at a time when an x-ray image was taken to provide for a better comparison of day-to-day improvement of the patient. More particularly and as described further herein, such methods, techniques and apparatus provide a visual display of the angulation of the patient to the radiologist, technician or like during the process associated with the taking of the x-ray image and also so that the x-ray image therefrom also includes a representation or display of the angulation of the patient. In this way, there is provided a permanent record of such angulation for each x-ray taken which can used by the physician, radiologist or the like in connection with the reading of such acquired x-ray images and in determining any treatment protocol and/or the effectiveness of such treatment protocol.

More specifically, the present invention, allows a movable object to roll freely within an enclosure in relation to an angle in which a cassette (and hence a patient) is placed. Because the cassette is placed parallel to a patient's back, the angle at which the cassette is placed is a direct translation of the angle in which the patient is positioned in relation to the ground and thus indicates the angle at which an x-ray image was taken. In order to correlate the position of the movable object in the modified enclosure with the angle at which the cassette is currently placed, a plurality of markers are protruded from the inner surface of a passageway within the modified enclosure. Based upon the position of the movable object in relation to a particular marker at the time an x-ray is taken, the user can identify the angulation at which the cassette is currently positioned, and therefore the angulation of the patient/object as well. That is, each of the plurality of markers represents a particular angulation of the cassette.

In one embodiment of the present invention, an apparatus and method for displaying an angle on an x-ray image includes a portable x-ray imaging device, an enclosure attached to the front surface of the cassette, a movable object, and a plurality of markers. In the present invention, the portable imaging x-ray device produces x-ray images of an object (e.g., a patient) between the x-ray device and a cassette. In order to determine the angulation at which the cassette is positioned in relation to the object, the enclosure is attached to a surface, more particularly, a front surface, of the cassette. The enclosure in this embodiment is modified to include a measurably defined passageway through which the movable object travels freely in a direction in relation to the angulation at which the cassette is currently to disposed. Protruding from an inner surface of the passageway is the plurality of markers, each of which positioned to correlate to a specific degree of angulation. Accordingly, when the movable object comes to rest, the position of the movable object in relation to a particular marker of the plurality of markers identifies the angulation at which the cassette is disposed, thus, identifying the angle of the cassette to a user, e.g., a technologist. The use of the term herein shall be understood to also include a technician and radiologist.

In some embodiments of the present invention, the movable object and the plurality of markers are made of a material which allows the movable object and the plurality of markers to be visible in an x-ray image that is produced by the x-ray machine. By doing so, users, e.g., technologists, can readily identify an angle at which the x-ray was taken so that they can reproduce such an angulation in subsequent examinations and therefore allow for a more accurate comparison of the patient's condition.

Advantageously, by providing an indicator which demonstrates the angulation of the x-ray, the technologist will have better way to obtain consistent angulation. That is, the present invention provides an indication of the exact angle of the cassette and patient being x-rayed rather than just supine and non-supine as is done in conventional imaging. Thus, the present invention would be useful for quality assurance over time with individual technologists, especially in hospitals with radiologic technology training programs. Because the present invention more accurately represents an angle at which the patient is positioned during a portable x-ray exam, improved comparisons of patient conditions can be made over time. Additionally, clinicians can better plan therapies based on these more precise comparisons and possibly prevent unnecessary CT (Computerized Tomography) exams, thereby preventing the patient from being exposed to unnecessary amounts of radiation, and unduly costly expenditures.

Other aspects and embodiments of the invention are discussed below.

DEFINITIONS

The instant invention is most clearly understood with reference to the following definitions:

As used in the specification and claims, the singular form "a," "an" and "the" include plural references unless the context clearly dictates otherwise.

As used herein, the term "comprising" or "including" is intended to mean that the compositions, methods, devices, apparatuses and systems include the recited elements, but do not exclude other elements. "Consisting essentially of," when used to define compositions, devices, apparatuses, systems, and methods, shall mean excluding other elements of any essential significance to the combination. Embodiments defined by each of these transition terms are within the scope of this invention.

The term USP shall be understood to mean U.S. Patent Number, namely a U.S. patent granted by the U.S. Patent and Trademark Office.

X-ray device as used in the specification and claims shall be understood to include any machine, hardware, or the like either portable or stationary for producing electromagnetic radiation with wavelengths between about 0.005 and 10 nm.

The term X-ray as used in the specification and the claims shall be understood to include but not limited to, an roentgen ray, x radiation or the like which produces electromagnetic radiation with wavelengths between about 0.005 and 10 nm and penetrate most substances, e.g., to investigate the integrity of certain structures and to make radiographic images for diagnostic purposes, as in radiography and fluoroscopy.

The term cassette, as used in the specification and claims shall be understood to mean but not be limited to a light-proof housing for x-ray film, including a front and a back intensifying screen, between which a film can be placed and held during exposure. The term cassette also shall be understood to include or comprise sensors, detectors or devices that are sensitive to, or can detect, electromagnetic radiation with wavelengths between about 0.005 and 10 nm and which sensors, detectors or devices can provide an electrical output or output signals representative of the detected radiation or image associated with such detected radiation.

The term CXR as used in the specification and the claims shall be understood to mean a chest x-ray which is an image of the thoracic cavity, produced by an irradiation scan of the upper torso.

The term specimen or subject shall be understood to expressly include, but not be limited to members of the animal kingdom, including vertebrates (preferably a mammal, more preferably a human); test specimens, such as biological tissue, for example, removed from such members of the animal kingdom; and inanimate objects or phantoms which can be imaged by x-ray techniques, or which contain water or sources of other sensitive nuclei. Mammals include, but are not limited to, mice, monkeys, humans, farm animals, sport animals, and pets.

The term patient shall be understood to include mammalians including human beings as well as other members of the animal kingdom.

The term effusions shall be understood to mean but not be limited to the escape of fluid, for example, from blood vessels as a result of rupture or seepage, usually into a body cavity, such as the chest or abdomen.

BRIEF DESCRIPTION OF THE DRAWINGS

For a fuller understanding of the nature and desired objects of the present invention, reference is made to the following detailed description taken in conjunction with the accompanying drawing figures wherein like reference character denote corresponding parts throughout the several views and wherein.

DETAILED DESCRIPTION OF THE INVENTION

Figure 1A:
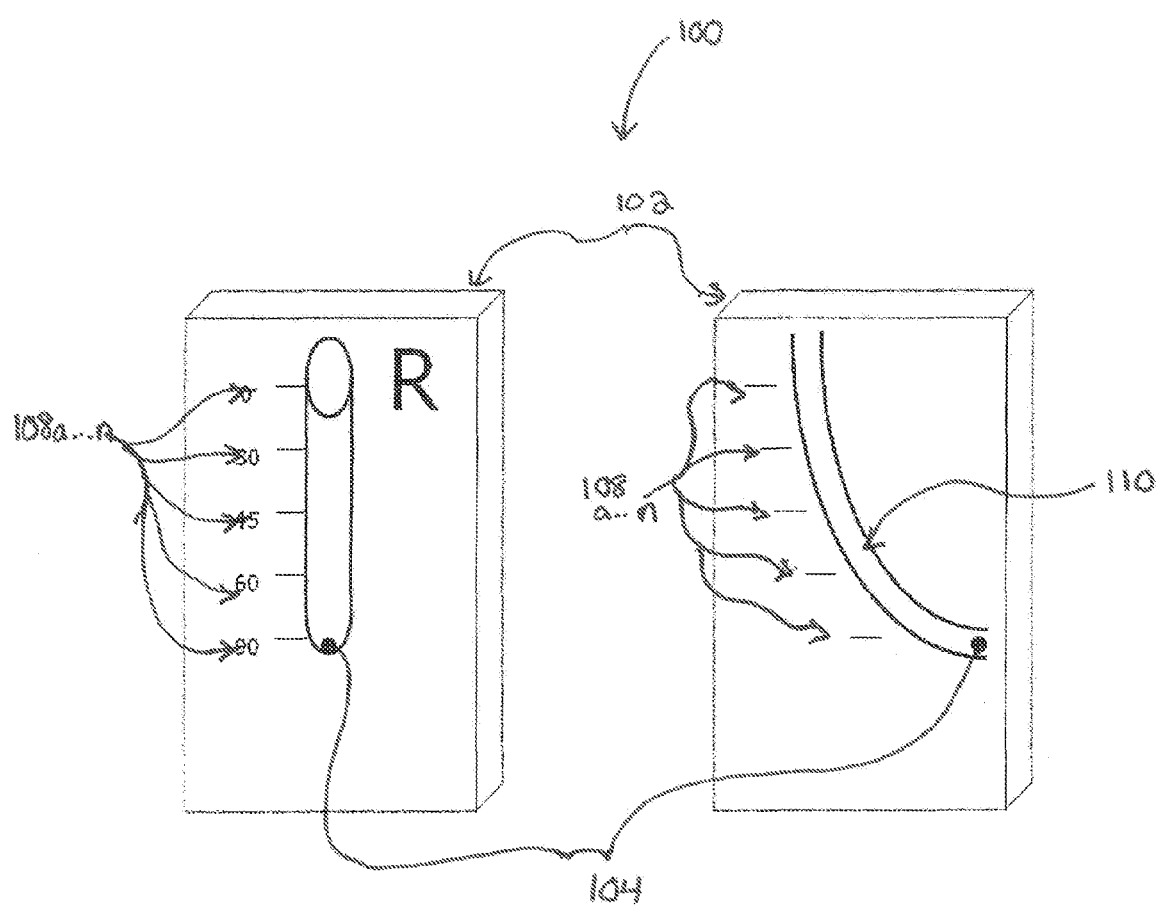
FIGS. 1A,B are diagrammatic front and side views illustrating two exemplary embodiments for displaying an angulation of a cassette in accordance the present invention, respectively.

Referring now to the various figures of the drawing wherein like reference characters refer to like parts, there is shown in FIG. 1A a schematic block diagram of an exemplary apparatus 100 for displaying the angulation at which a cassette is positioned, herein also referred to as an "x-clometer" or "xCline." It should be recognized that the described system is not limiting as it is within the skill of those knowledgeable in the art to adapt other systems (e.g., systems that appertain to other than just portable chest x-rays and the like) to function and operate as described herein.

The present invention provides methods, techniques and apparatus for displaying an angulation of a patient and the x-ray machine at a time when an x-ray image is taken to provide for a better comparison of day-to-day improvement of the patient. More particularly, such methods, techniques and apparatus provide a visual display of the angulation of the patient to the radiologist, technician or like during the process associated with the taking of the x-ray image and also so that the x-ray image resulting therefrom also includes a representation or display of the angulation of the patient. In this way, there is provided a permanent record of such angulation for each x-ray taken which can used by the physician, radiologist or the like in connection with the reading of such acquired x-ray images and in determining any treatment protocol and/or the effectiveness of such treatment protocol.

More specifically, the present invention, allows a movable object to roll freely within an enclosure in relation to an angle in which a cassette for an x-ray device, e.g., a portable x-ray device, is placed. Since the cassette is placed parallel to a patient's back, the angle at which the cassette is placed is a direct translation of the angle in which the patient is positioned in relation to the ground and thus indicates the angle at which an x-ray image was taken. In order to correlate the position of the movable object in the modified enclosure with the angle at which the cassette is currently placed, a plurality of markers are protruded from the inner surface of a passageway within the modified enclosure. Based upon the position of the movable object in relation to a particular marker at the time an x-ray is taken, the user can identify the angulation at which the cassette is currently positioned, and therefore the angulation of the patient/object as well.

In one embodiment of the present invention the present invention an apparatus and method for displaying and transmitting an angle on an x-ray image includes an x-ray device, an enclosure attached/mounted to the front surface of the cassette, a movable object, and a plurality of markers. The x-ray device is configured to produce x-ray images of an object (e.g., patient) between the x-ray device and a cassette. In order to determine the angulation at which the cassette is positioned in relation to the object, the enclosure is attached to a surface, more particularly a front surface, of the cassette.

The enclosure in the in this embodiment is modified to include a measurably defined passageway through which the movable object travels freely in a direction in relation to the angulation at which the cassette is currently disposed. Protruding from an inner surface of the passageway is the plurality of markers, each of which positioned to correlate to a specific degree of angulation. Accordingly, when the movable object comes to rest, the position of the movable object in relation to a particular marker of the plurality of markers identifies the angulation at which the cassette is disposed, thus, identifying the angle of the cassette to a user, e.g., a technologist.

FIG. 1A illustrates an exemplary apparatus/x-clometer in accordance with an illustrative embodiment the present invention. The x-clometer 100 includes an enclosure 102, a movable object 104, a means of mounting (not shown) to said enclosure 102, and a plurality of markers 108. More particularly, the movable object 104 is disposed in a modified passageway 110 within the enclosure 102 so that the movable object moves freely in a direction in relation to the angulation at which the cassette is currently disposed. The movable object may be embodied as, e.g., a ball or disk that rotates through the modified passageway. The enclosure 102, for example, can be formed as a modified cylinder and made of a clear transparent material, e.g., plastic, in order to allow a user to visualize the movement of the movable object 104 through the passageway 110 in the enclosure 102. The enclosure 102 is mounted on a cassette (not shown) used with, e.g., a portable x-ray device in creation of x-ray images during, e.g., a portable chest x-ray (CXR) exam. Although the enclosure 102 can be mounted in any position on the cassette, preferably, the enclosure should be mounted flushly to ensure the most accurate reading possible.

The plurality of markers 108a . . . n are positioned in the modified passageway 110 at predetermined increments sufficient to allow angulation differentiation between a plurality of angles at which a cassette is positioned, (e.g., 0, 30, 45, 60 or 90 degrees). As mentioned above, the enclosure 102 in which the passageway 110 resides can be a modified enclosure and a modified passageway specifically. In a particular embodiment, the passageway 110 is formed in a somewhat parabolic shape defined by one or more mathematical equations, which confines the movable object to a back and forth direction of movement. That is, for example when the movable object is a ball, the circumference of the passageway may be, for example, circular in nature. On the other hand, when the movable object is a disk, the passageway may be shaped in a way which allows the disk to travel through the passageway without falling over.

In one embodiment of the present invention, the passageway, in which the movable object is allowed to freely move, is formed in an upwardly vertical direction from the bottom end of the enclosure to an upper end of the enclosure in a predetermined curvature pattern. The predetermined curvature pattern is calculated to create a path which positions the movable object in a location within the passageway 110 so that the position of the movable object directly corresponds to a vertical angulation of the cassette on which the enclosure is mounted. Thus, the movable object is allowed to move freely in the vertical direction, but minimally in the horizontal direction. More specifically, the angle of inclination is quantified by a movable object/ball bearing settling in a curved tube in relation to various markers thereby indicating the angle of inclination of the cassette and thus the patient as well.

Figure 1B:
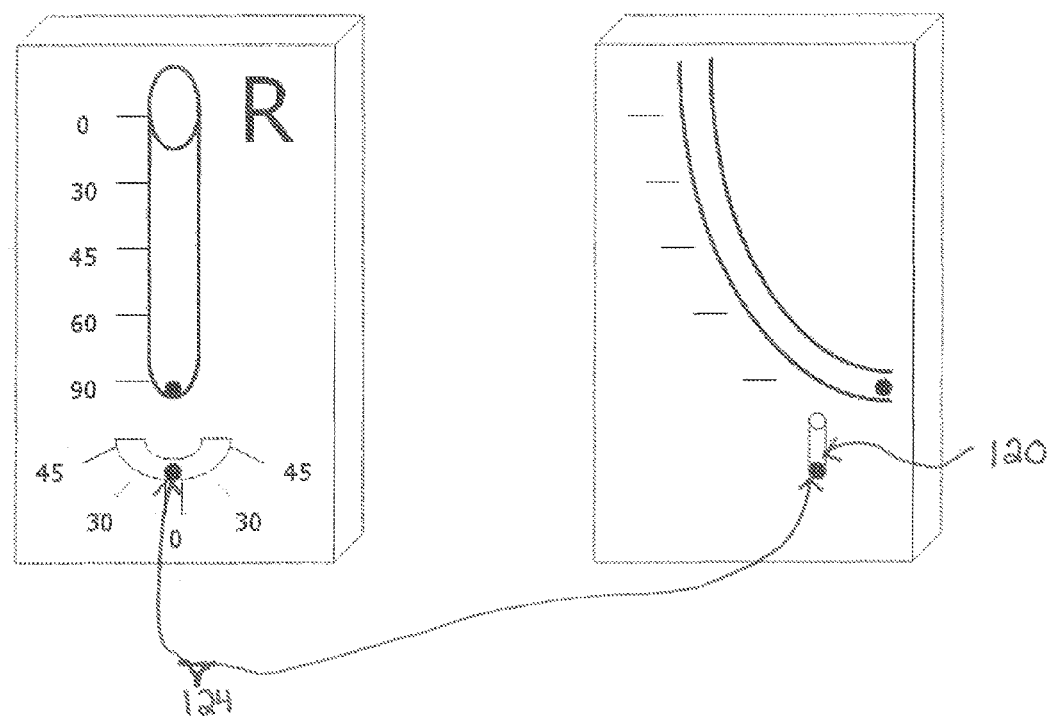

In yet other embodiments of the present invention and now referring to FIG. 1B, the present invention can also include a second passageway 120 in which a second movable object 124 is allowed to freely move from side to side in relation to the horizontal angulation of the cassette. In this embodiment, the second passageway can be formed, for example, in an upwardly "U" like fashion. Again the exact form of the second passageway 120 is calculated as a curvature pattern that provides a path which positions the second movable object 124 in a location within the second passageway 120 which directly corresponds to the horizontal angulation of the cassette.

Additionally, the movable object and the plurality of markers are made of a radiopaque material which are visible on a resulting x-ray image taken by the x-ray device. For example, the movable object 104 would visibly intersect various markers which correlate directly to a particular angulation. That is, the movable object and each of the plurality of markers are visible on the resulting x-ray image in a way which allows the technologist to identify the angle at which the x-ray was taken.

It should be understood that the position of the movable object 104 in the passageway 110 is different depending on the angulation of the cassette even though it can look the same on the x-ray image itself. For example, FIGS. 2A,B illustrates various side views of the apparatus/x-clometer when the x-clometer is placed at various angulations. As can be seen from FIGS. 2A,B the movable object moves up and down the passageway 110 in relation to the vertical angulation of the cassette in which the enclosure 102 is mounted. The arrows in each view correspond to the direction in which the x-rays are traveling. Illustratively, the plan view is the view which is seen from the x-ray device and the profile view is the view which is seen from the side of the cassette. As can be seen from the FIG. 2A,B, the movable object 104 is at a first end when the cassette is positioned at a 90 degree angle. In contrast, the movable object 104 is at a second or distal end when the cassette is positioned at 0 degrees.

Figure 3:
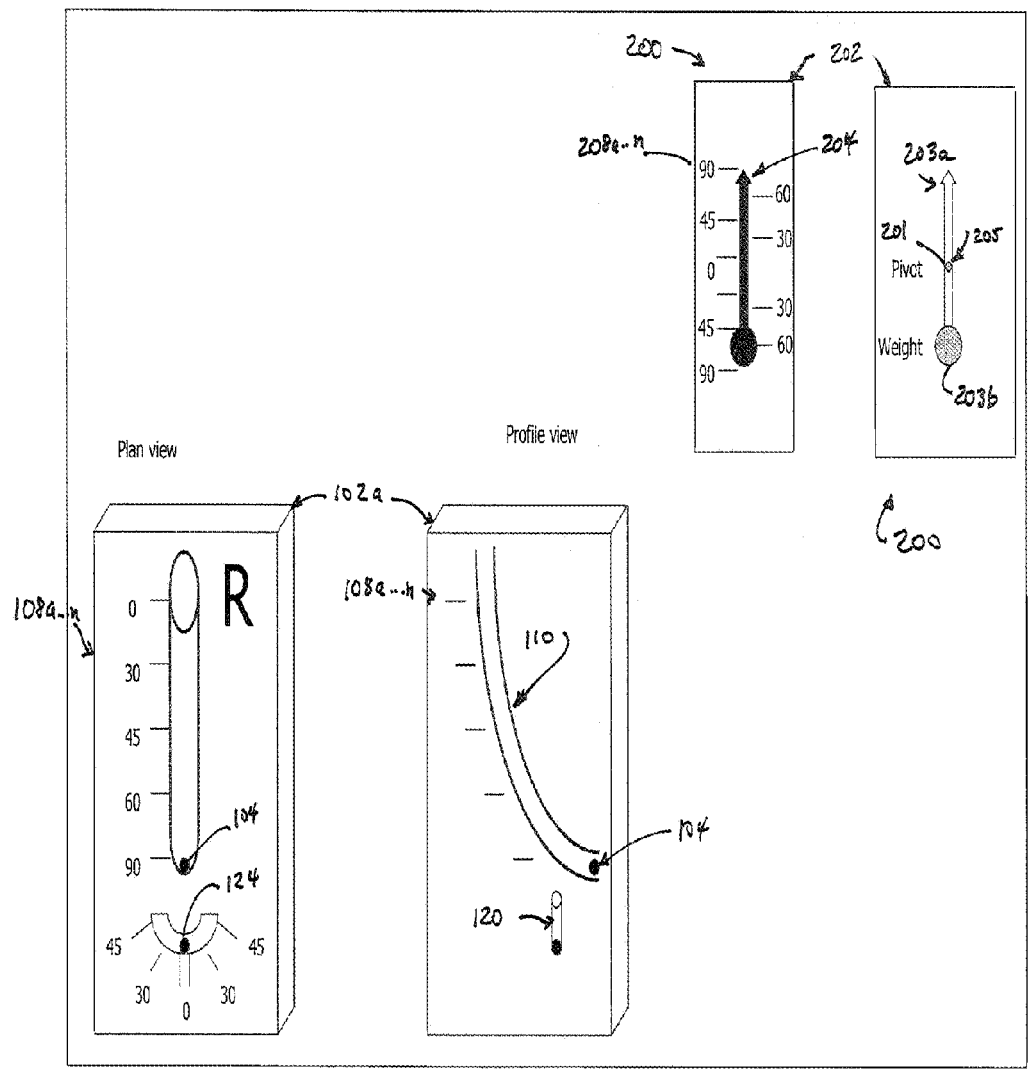
FIG. 3 provides diagrammatic front and side views illustrating other exemplary embodiments for displaying an angulation of a cassette in accordance the present invention, respectively.

In yet further embodiments, and with reference to FIG. 3, there is shown another exemplary illustrative apparatus 200 according to the present invention that can be used alone, or in combination with any of the apparatus 100 embodiments shown in FIGS. 1A,B. Such an apparatus 200 includes an enclosure 202, a movable pointing object 204, a means of mounting (not shown) to the enclosure 202 and a plurality of markers 208 (208 a . . . n). More particularly, the movable pointing object 204 is pivotatbly disposed within the enclosure 202 and configured so that the movable pivoting object freely pivots within the enclosure about a pivot point in a direction in relation to the angulation at which the cassette is currently disposed and with respect to gravity.

In a particular embodiments, the movable object 204 includes a first end 203a, a second end 203b, and a pivot aperture or opening 205 in the movable object. The enclosure also is configured so as to include a pivot 201 or pivoting structure which is received in the pivot aperture or opening 205. In particular embodiments, the first end 203a of the movable pointing object 204 is configured and arranged so that it combination with the markings 208a . . . n provides an indication of the vertical angulation of the cassette as described further herein. In a particular illustrative embodiment, the first end 203a is configured and arranged so as to present a structure (e.g., an arrowhead type of structure) that points to the marking corresponding to the vertical angulation of the cassette.

In particular embodiments, the second end 203b of the movable pointing object 204 is configured and arranged so that the movable pointing object 204 pivots about the pivot 201 of the enclosure 202 responsive to vertical angular movement of the cassette. In particular illustrative embodiments, the second end 203b is weighted (e.g., includes a weight) such that the movable pointing object 204 is maintained in a given orientation by gravity (e.g., maintained in vertical or upright direction by gravity).

The enclosure 202, for example, is formed in any of a number of structures known in the art (e.g., a box like structure) that are otherwise appropriate for the intended use. Such an enclosure preferably is made of a clear transparent material, e.g., plastic, in order to allow a user to visualize at least the first end 203a of movable pointing object 204 through the enclosure 202 as the movable pointing object pivots within the enclosure. As indicated herein, such an enclosure 202 is mounted on a cassette (not shown) used with, e.g., a portable x-ray device in creation of x-ray images during, e.g., a portable chest x-ray (CXR) exam. Although the enclosure 202 can be mounted in any position on the cassette, preferably, the enclosure should be mounted flushly to ensure the most accurate reading possible.

In yet further embodiments, the enclosure 202 of this embodiment also is configurable so as to include the second passageway 120 described herein in which a second movable object 124 is allowed to freely move from side to side in relation to the horizontal angulation of the cassette. As also indicated herein, any of the apparatuses/embodiments described herein and shown in FIGS. 1A,B also can be mounted in any position on the cassette, preferably, the enclosure should be mounted flushly to ensure the most accurate reading possible. In this way, redundant information as to the vertical angulation of the cassette or redundant information as to the vertical angulation of the cassette and the horizontal angulation of the cassette can be obtained in combination with the vertical angulation of the cassette as shown using the apparatus of FIG. 3.

The enclosure 202 also is configurable so as to include a plurality of markers 208a . . . n that are arranged at predetermined increments sufficient to allow angulation differentiation between a plurality of angles at which a cassette is positioned, (e.g., 0, 30, 45, 60 or 90 degrees). In a particular exemplary embodiment, these markers are provided in a surface of the enclosure 202 and positioned with respect to the movable pointing object 202 such that the vertical angular position of the cassette can be determined by the first end 203 pointing to one of the markers corresponding to the vertical angular position of the cassette. In other words, as the enclosure moves vertically with the cassette and thus also the patient, and as the movable pointing object pivots within the enclosure to maintain its orientation with respect to gravity/ground, the first end 203a moves to a position corresponding to the vertical angulation of the cassette.

As indicated herein, the movable pointing object 204 and the plurality of markers 208 a . . . n are made of a radiopaque material that are visible on a resulting x-ray image taken by the x-ray device. For example, the movable pointing object 204 would be shown as pointing to one of the various markers that correlates to a particular angulation. That is, the movable pointing object 204 and each of the plurality of markers would be visible on the resulting x-ray image in a way which allows the technologist to identify the angle at which the x-ray was taken. While the physical length of the movable pointing object 204 does not change, as the x-rays will be incident upon the movable pointing object, the movable pointing object will have a different length in the x-ray image and thus point at the appropriate vertical angle.

Figure 4A:
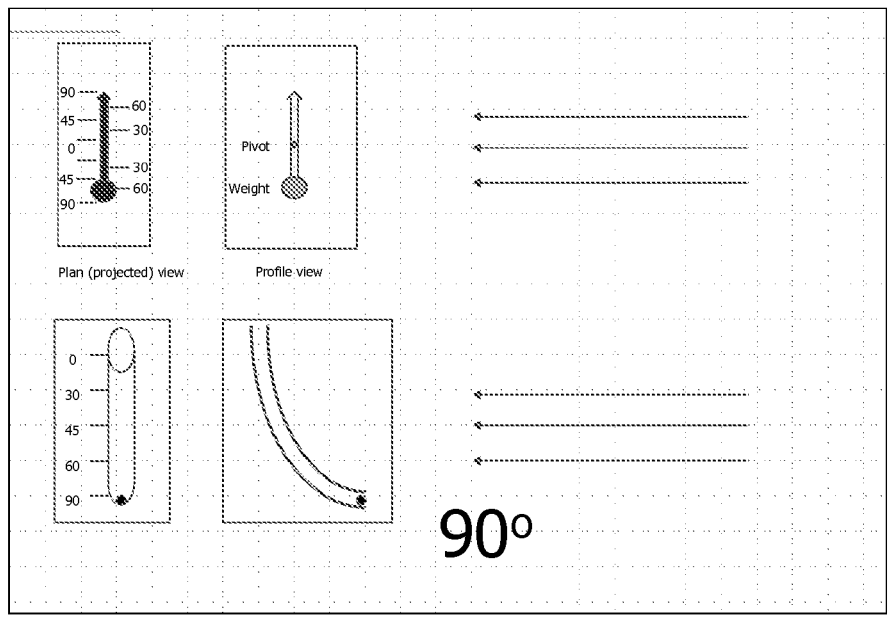
FIGS. 4A-C respectively are diagrammatic views illustrating the exemplary apparatus of FIG. 3 at various angles.
Figure 4A:
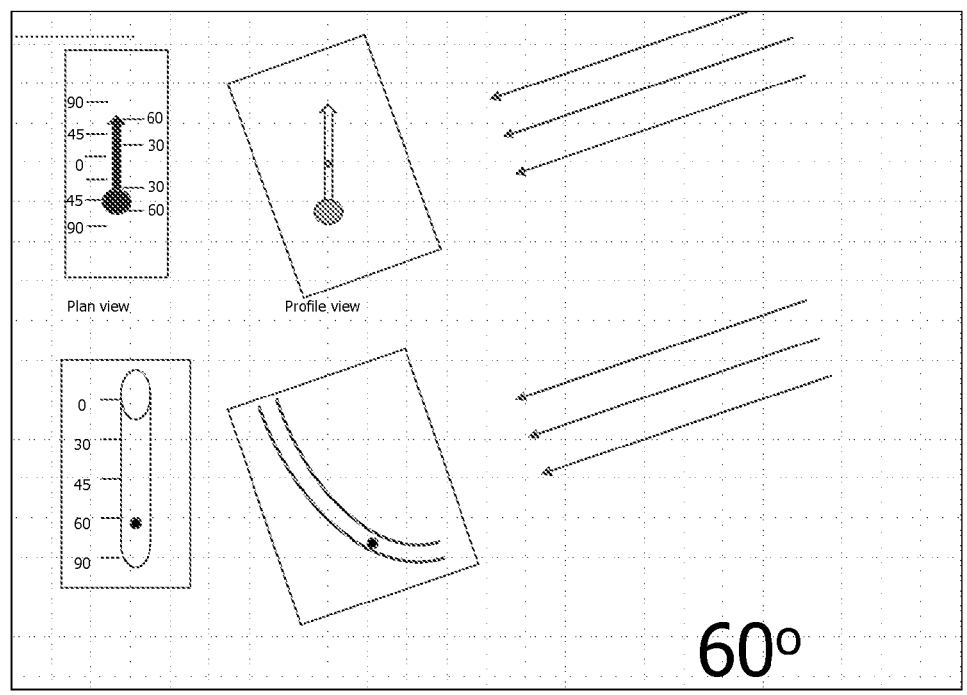
Figure 4B:
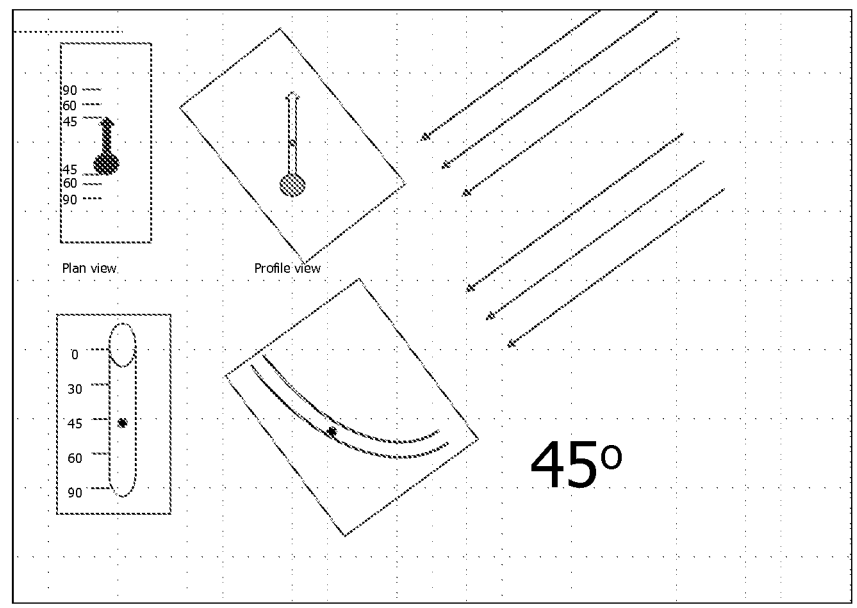
Figure 4B:
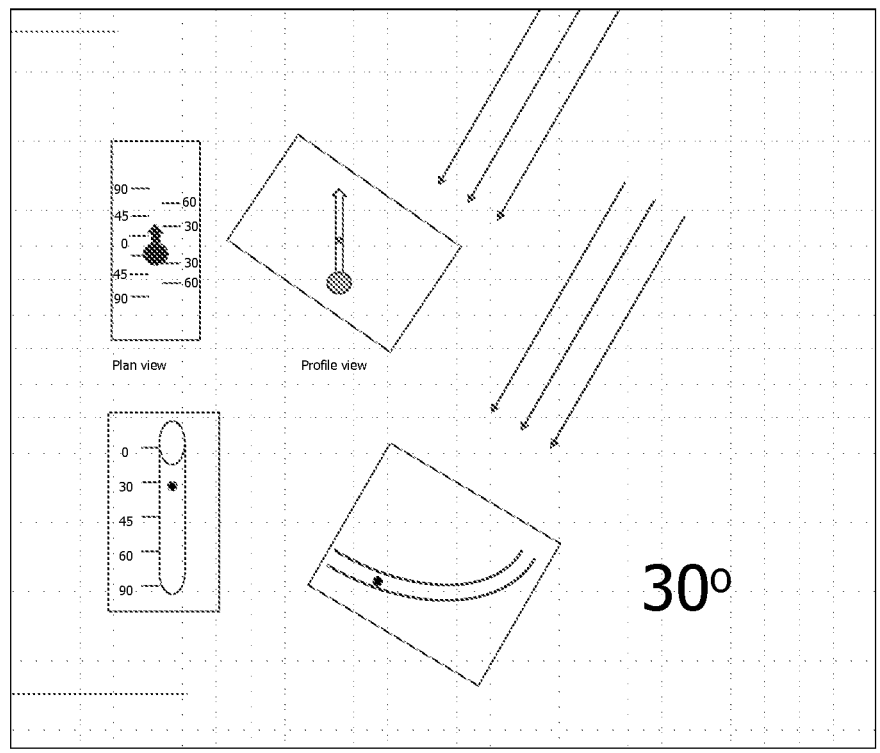
Figure 4C:
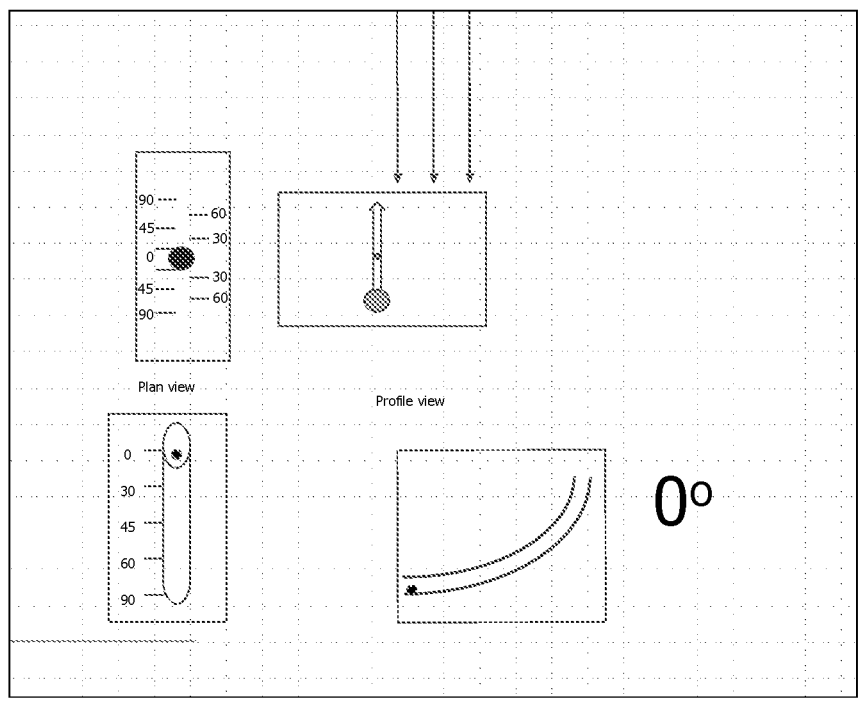

Referring now to FIGS. 4A-C there is shown/illustrated various side views of the apparatus 200 when it or the cassette is placed or positioned at various angulations. As can be seen from FIGS. 4A-C the movable pointing object 204, more specifically the first end 203a thereof moves up and down the markers 208 in relation to the vertical angulation of the cassette to which the enclosure 202 is mounted. The arrows with lines in each view correspond to the direction in which the x-rays are traveling. Illustratively, the plan view is the view which is seen from the x-ray device and the profile view is the view which is seen from the side of the cassette. As can be seen from these figures the first end 203a of the movable pointing object 204 is upright and points to the 90 degree marker when the cassette is positioned at a 90 degree angle as shown in FIG. 4A (top figure).

In contrast, when the cassette is positioned at 0 degrees (supine position of the patient) the first end 203a of the movable pointing object 204 effectively mergers with the structure of the second end 203b such that the second end structure is disposed opposite to the 0 degree marker(s). For example, if the second end 203b is in the form of a spherical structure, a circular object will appear proximal the 0 degree marker(s) as shown in FIG. 4C. In the case of angles between 90 and 0 degrees, as shown in FIGS. 4A-B, the first end 203a of the movable pointing object points to the angle that correlates to the vertical angulation of the cassette.

Advantageously, by providing an indicator which demonstrates the angulation of the x-ray, a technologist will have a better way to obtain consistent angulation. That is, the present invention provides an indication of the exact angulation of the cassette and patients being x-rayed, rather than just supine and non-supine as is done in conventional imaging. Thus, the present invention would be useful for quality assurance over time with individual technologists, especially in hospitals with radiologic technology training programs. Because the present invention more accurately represents an angle at which a patient or object is positioned during, e.g., a portable x-ray exam, improved comparisons of patient conditions can be made over time.

Additionally, clinicians can better plan therapies based on these more precise comparisons and possibly prevent unnecessary CT (Computerized Tomography) exams, thereby preventing patients from being exposed to unnecessary amounts of radiation. In short, the present invention quantifies any of a number of angles of inclination; whereas prior devices only indicate supine or not supine or are overly complex to make and use. Thus, use of the present invention will help save lives through improved diagnosis and more objective comparison of effusions.

Even further, in embodiments where this device is applied to alternative types of exams, for example, abdomen exams, interdepartmental abdomen exams can also benefit from use of this device as not all department exams are done erect, however, the technologist can falsely indicate (e.g., with an arrow pointing up, or an "erect" marker) that the film was taken upright. From an epidemiological perspective, once the above described invention is available and widely used literature dictating population metrics describing average upright angles for particular angles could be distributed to achieve, and derive an expected degree of erect projection for a patient received a particular type of x-ray exam.

EXAMPLE

A prototype was constructed and tested under a number of different conditions so as to determine/demonstrate the effectiveness of the prototype to provide an indication of the angulation of the test subject as well as the ability to provide such an indication of angulation repetitively. As described further herein, a conventional marker including three small balls in a bubble was used to assess the performance of the prototype as well as to illustrate the effectiveness of the prototype as compared to the conventional marker.

Methods and Materials

Figure 5A:
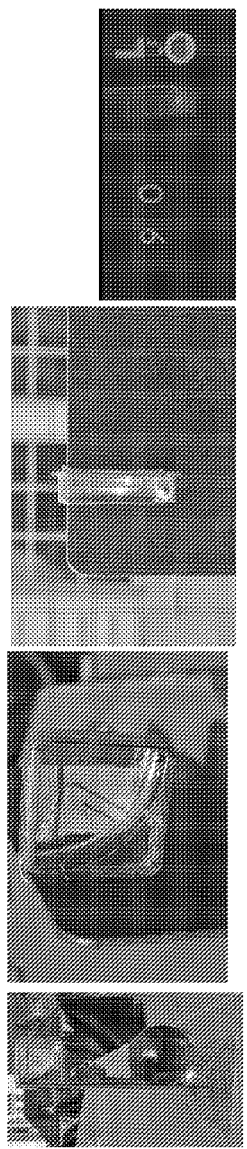
FIGS. 5A-C provide various illustrative views of an illustrative construction of a proof of concept prototype of the device/apparatus of the present invention and an illustration that is representative of a patient being located in an upright or 90 degree position (FIG. 5A); of a patient being located at a 50 degree position (FIG. 5B) and of a patient being located at a 20 degree position (FIG. 5C)
Figure 5B:
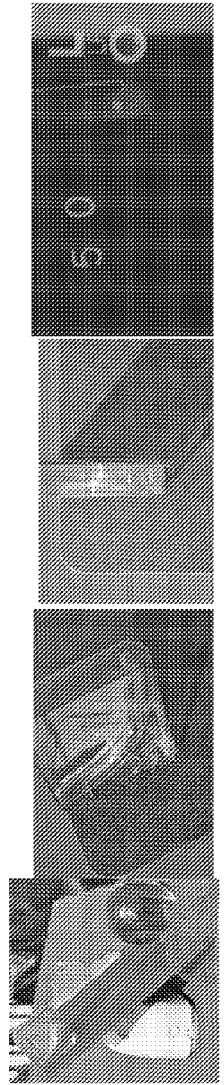
Figure 5C:
Figure 5D:
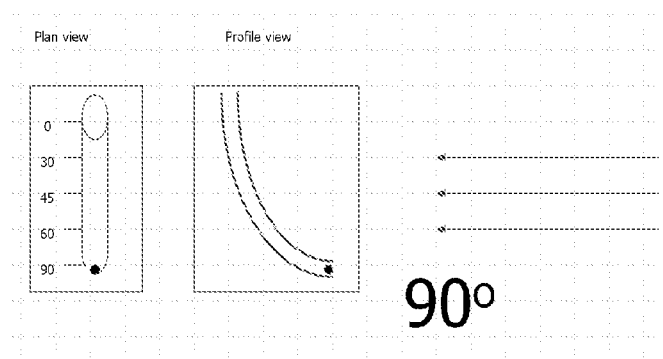
FIG. 5D provide various illustrative views illustrating locating the prototype at various cassette angulations or inclinations.
Figure 5D:
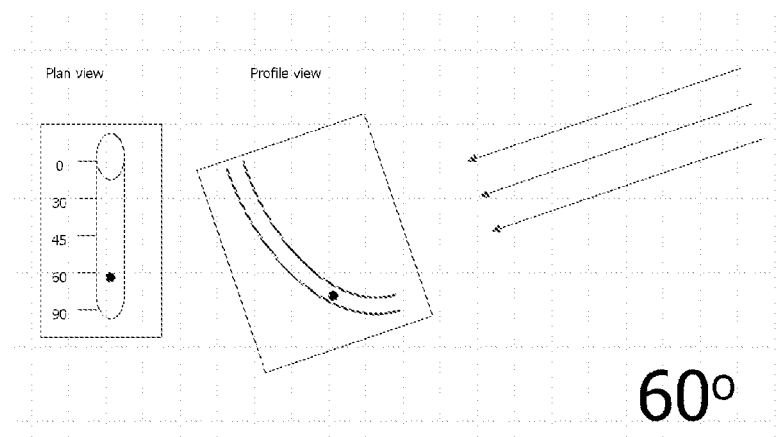
Figure 5D:
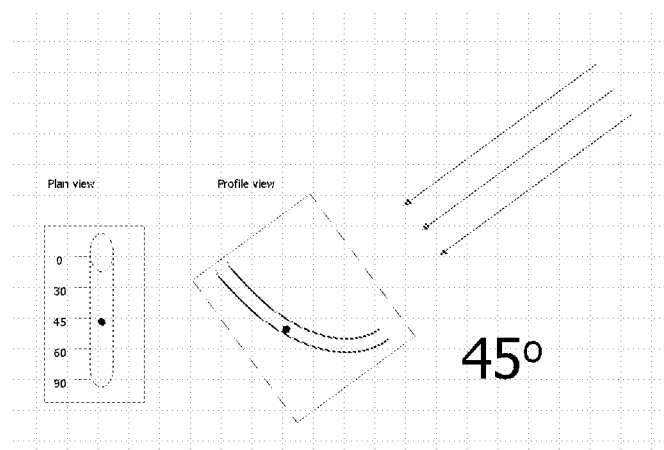
Figure 5D:
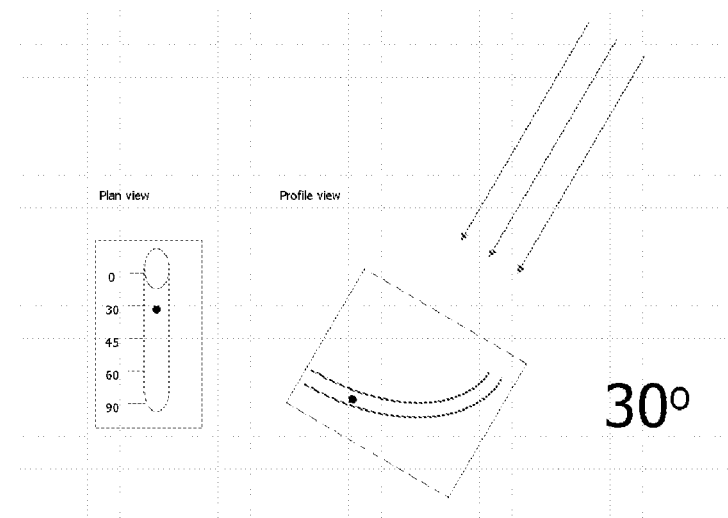
Figure 5D:
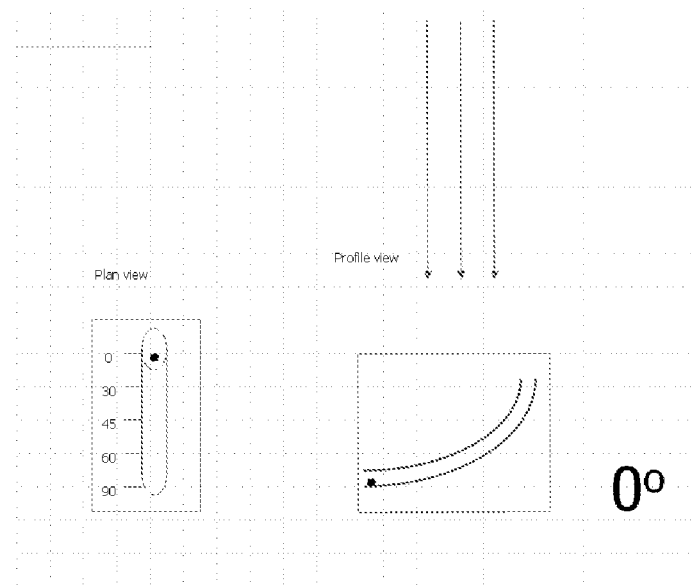

Referring now to FIGS. 5 A-C, there is shown various illustrative views of an illustrative construction of a proof of concept prototype of the device/apparatus of the present invention and an illustration that is representative of a patient being located in an upright or 90 degree position (FIG. 5A); of a patient being located at a 50 degree position (FIG. 5B) and of a patient being located at a 20 degree position (FIG. 5C). Various illustrative views illustrating locating the prototype at various cassette angulations or inclinations are provided in FIG. 5D.

Such a prototype includes a curved plastic tube or cylinder, a steel ball (e.g., a BB) and a multiplicity of paper clips used to form markers as herein described. The clear plastic tube is radio-transparent and also was made so as to allow the ball to roll or rotate freely within the tube. As the plastic tube is clear, this allows the technologist to visualize and/or verify movement of the ball within the tube. The paper clips were cut and secured (e.g., taped) to the tube and along the circumference of the tube in increments sufficient to allow angle differentiation for specified angles including for example, 0, 10, 20, 30, 40, 50, 60, 70, 80 and 90 degrees. As the paper clips are radiopaque, the paper clips form angle reference marks. In the prototype, the ball in the tube/cylinder falls to location that when imaged by an x-ray aligns with one of the reference markers and thus provides a visual indication of the angulation of the prototype.

Figure 6:
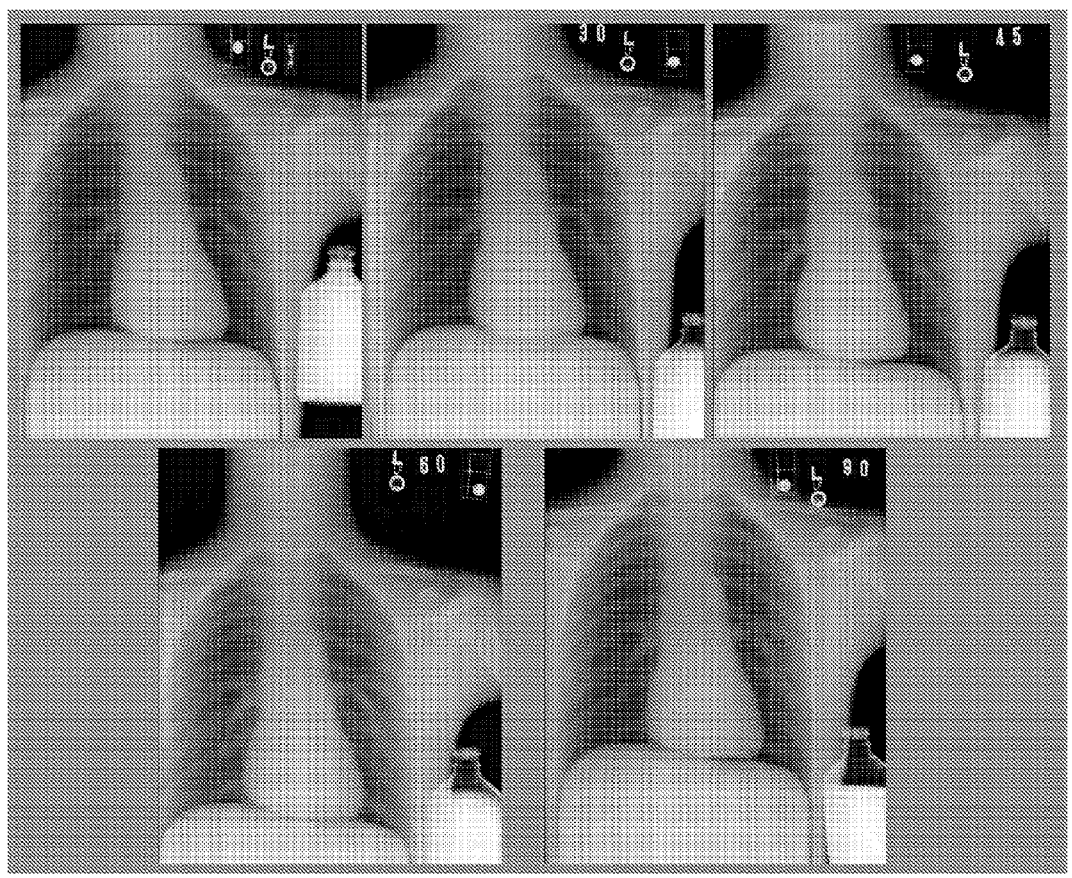
FIG. 6 provides various illustrative X-rays of resultant CXRs of a phantom and contrast as well as the proof of concept prototype.
Figure 7A:
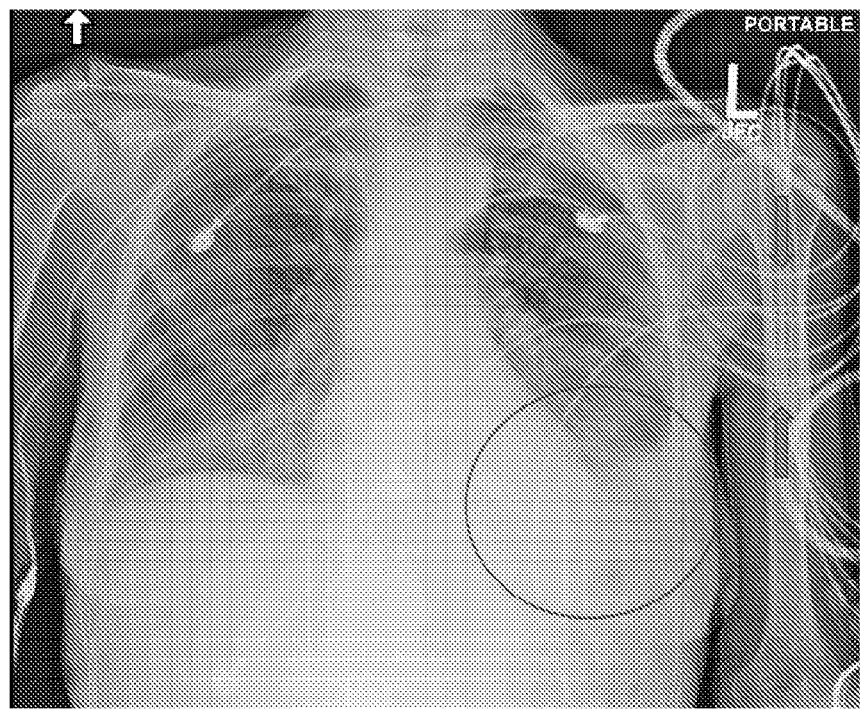
FIGS. 7A, B are exemplary images showing conventional images taken by a portable x-ray on two different occasions.
Figure 7B:
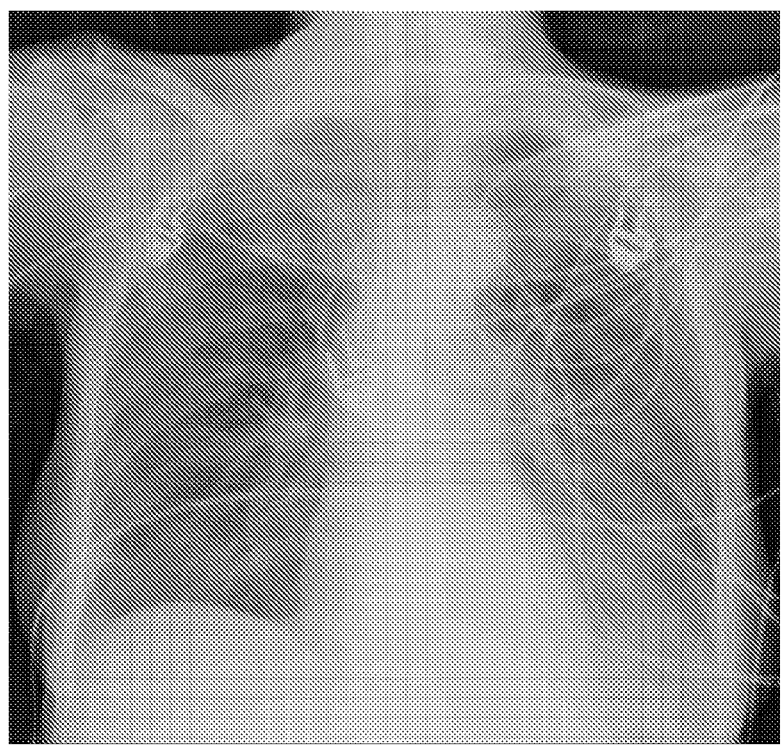

The prototype was evaluated in a proof of concept setting, a laboratory setting and a clinical setting. In either setting the prototype was used in combination with an existing or conventional marker, including three small balls in a bubble. In the proof-of-concept setting x-ray images (see FIG. 6) were acquired of a phantom having the torso of a human body, a contrast agent in a bottle, using a cassette where the prototype and a conventional marker were affixed to the cassette as described herein so that the prototype would be imaged along with the phantom and also provide a display or reading of the angulation of the phantom.

The acquired x-rays images show dispersion of fluid at 0, 45 and 90 degree angles. In this regards, note the air-fluid level on the 90 degree (upright or erect) projection—the lower right image. Also note that most dispersion on the supine (o degree projection. The visual prototype reflect the various degrees by overlap of the metal ball and the metallic clips (i.e., paper clips affixed to the tube). The supine image shows the ball between two paper clip markers, on the 45 degree angle the paper clip bisects the ball, and for the other angles ⅓ of the ball (top or bottom). As to the conventional marker (i.e., left marker, with three lead balls) show the three balls distributed in the center of the bubble on the supine projections and on all others the balls fell to the dependent position.

Figure 2A:
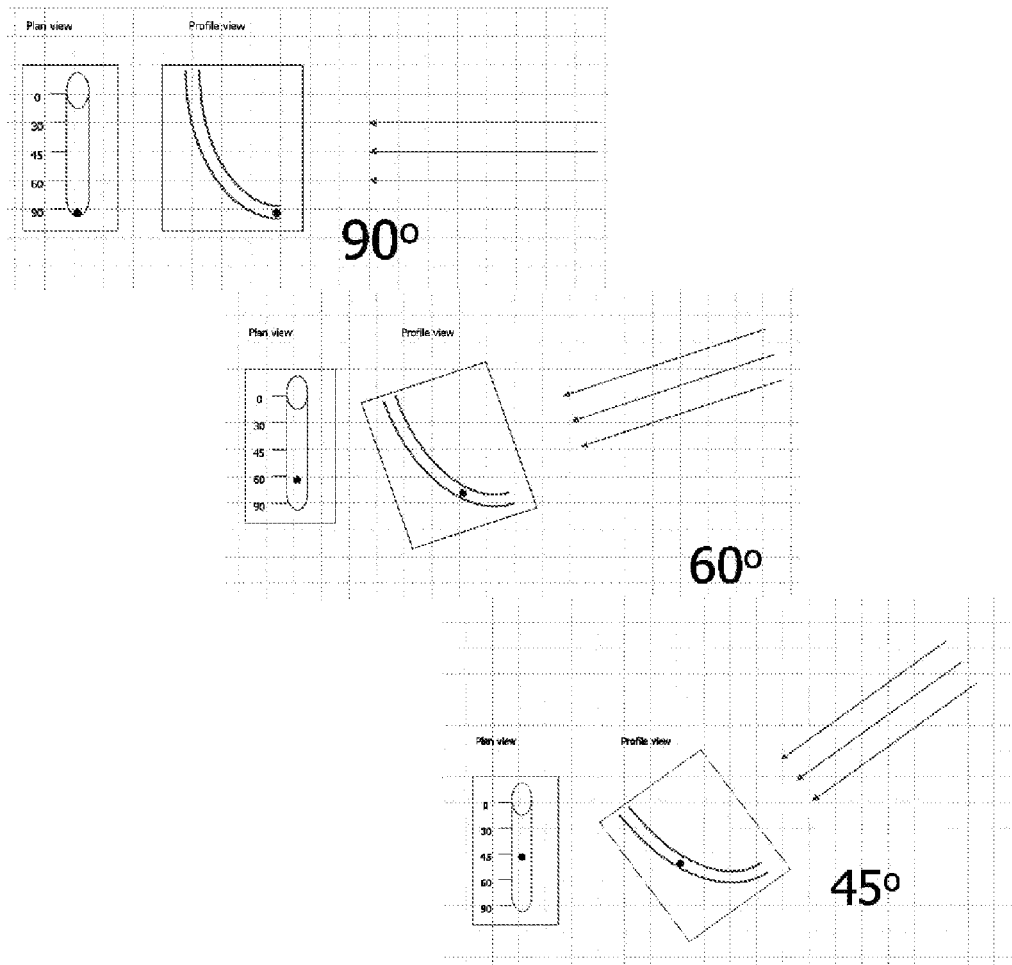
FIGS. 2A,B respectively are diagrammatic views illustrating the exemplary apparatus of FIGS. 1A,B at various angles.
Figure 2B:
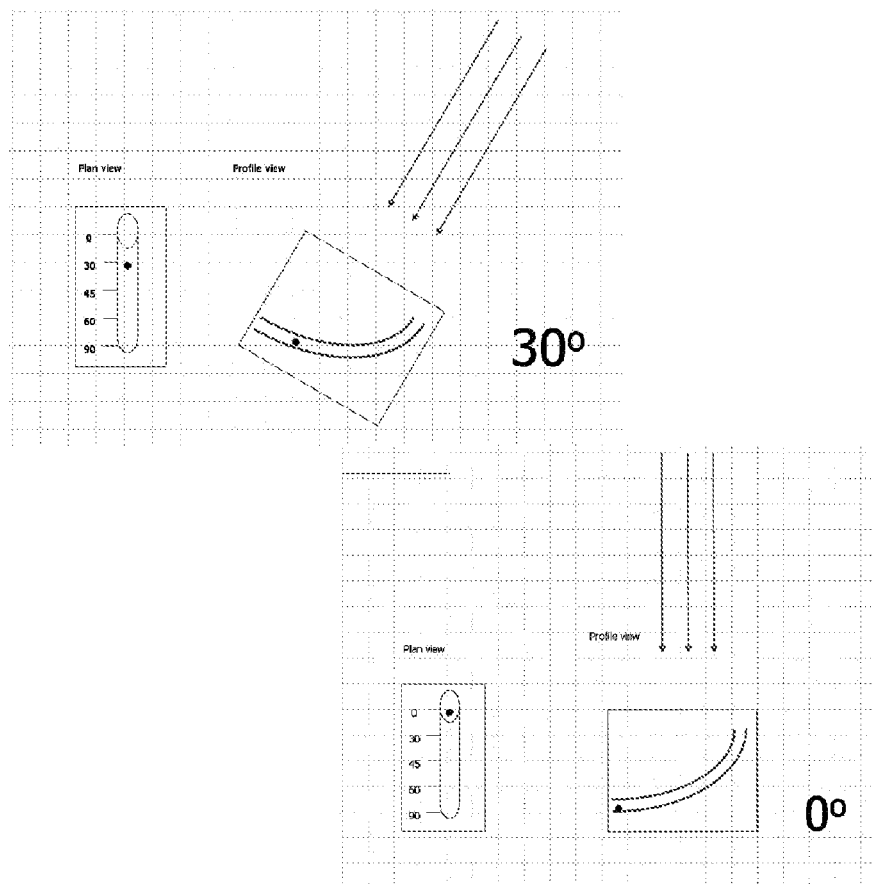

In the laboratory setting, such as shown in FIGS. 2A,B, three observers estimated the degree of inclination. Also, the device or prototype and the conventional marker were imaged at 10 degree increments between and including 0 and 90 degrees. In the laboratory setting, the prototype demonstrated that the accuracy of the prototype was within 10 degrees on 28 of the 30 observations. For the remaining two observations, the prototype's accuracy was within 20 degrees. These two observations are associated with the imaging of the prototype at 20 degrees.

In the laboratory setting, the conventional marker only differentiated supine versus non-supine. At 30 degrees of inclination, the conventional marker was already indicating "upright" and kept that position for angles of 30 to 90 degrees.

In the clinical setting one radiologist estimated the degree of inclination on 25 portable chest x-rays in which the prototype was affixed to the cassette. Based on the preliminary results, it was estimated that accuracy was within 10 degrees.

In sum, the study demonstrated that the prototypes can be seen on the radiography and it was believed that this occurred because of the metallic ball and the metallic markers (paper clips affixed to the tube/cylinder). It also was demonstrated the prototypes provided a objective indication of inclination as compared to the conventional markers.

EQUIVALENTS

Those skilled in the art will recognize, or be able to ascertain using no more than routine experimentation, many equivalents of the specific embodiments of the invention described herein. Such equivalents are intended to be encompassed by the following claims. For example, the present invention is described as being implemented along with a CXR, it will be apparent to those skilled in the art that the present invention can also be implemented in other forms of x-ray machines for examination of other areas of the body.

What is claimed is:

1. An apparatus for displaying an angulation on an x-ray image, the apparatus comprising:
   an x-ray device configured to produce x-ray images of an object between the x-ray device and a cassette;
   an enclosure attached to a surface of the cassette, the enclosure having a first passageway within the enclosure through which a first movable object travels in relation to an angulation at which the cassette is currently disposed, and the enclosure having a second passageway within the enclosure through which a second movable object travels in relation to the angulation at which the cassette is currently disposed;
   a first plurality of markers positioned adjacent to the first passageway through which the first movable object travels, wherein a position of the first movable object in relation to the first plurality of markers represents a first angle at which the object is positioned at a time when the x-ray image is taken; and
   a second plurality of markers positioned adjacent to the second passageway through which the second movable object travels, wherein a position of the second movable object in relation to the second plurality of markers represents a second angle at which the object is positioned at a time when the x-ray image is taken;
   wherein the first and second angles are defined in respective perpendicular planes; and
   wherein the first and second movable objects and the first and second pluralities of markers are visible on the x-ray image produced by the x-ray device.

2. The apparatus of claim 1, wherein the first passageway is measurably defined to provide a direct correlation with the angulation of the cassette when the first movable object travels through the first passageway.

3. The apparatus of claim 1, wherein the first measurably defined passageway is formed so as to allow the first movable object to move freely in a vertical direction along the first passageway.

4. The apparatus of claim 1, wherein the second movable object is allowed to freely move from side-to-side within the second passageway in relation to a horizontal angulation of the cassette, wherein the position of the second movable object in relation to the second passageway identifies a horizontal angulation of the cassette when the x-ray image is taken.

5. The apparatus of claim 1, wherein the first movable object is a ball and wherein the ball and the first plurality of markers are made of a material that is radiopaque.

6. The apparatus of claim 1, wherein the first movable object is a disk and wherein the disk and the first plurality of markers are made of a material that is radiopaque.

7. The apparatus of claim 1, wherein the enclosure is made of a transparent material so that the position of the first movable object relative to the first passageway is visible to a user.

8. The apparatus of claim 1, wherein the first passageway forms a first arcuate path in which the first movable object travels, and the second passageway forms a second arcuate path in which the second movable object travels, and the first and second arcuate paths define two respective planes that are perpendicular to each other.

9. The apparatus of claim 1, wherein the first passageway has a parabolic shape.

10. The apparatus of claim 1, wherein the first passageway curves about 90° from a first end of the first passageway to a second end of the first passageway.

11. A method for determining an angulation of an object in an x-ray image, the method comprising:
positioning a cassette of an x-ray device adjacent to an object at an angulation, wherein an enclosure is coupled to the cassette and the enclosure comprises a first passageway with a first movable object allowed to travel within the first passageway and the enclosure comprises a second passageway with a second movable object allowed to travel within the first passageway, the first passageway being disposed in a first plane and the second passageway being disposed in a second plane that is perpendicular to the first plane;
producing an x-ray image of the object at the angulation using the x-ray device, such that the positions of first and second movable objects relative to the first and second passageways, respectively, are shown in the x-ray image; and
identifying the angulation at which the object is positioned in the produced x-ray image by:
determining a first angle of the angulation based on the position of the first movable object relative to the first passageway shown in the produced x-ray image; and
determining a second angle of the angulation based on the position of the second movable object relative to the second passageway shown in the produced x-ray image.

12. The method of claim 11, wherein the first passageway allows the first movable object to move freely in a vertical direction and the second passageway allows the second movable object to move freely in a horizontal direction.

13. The method of claim 11, wherein the first movable object and the second movable object are balls.

14. The method of claim 11 wherein the x-ray device is a portable chest x-ray device.

15. The method of claim 11, wherein the enclosure is made of a transparent material so that the positions of the first and second movable objects are visible to a user.

16. The method of claim 11, wherein the first and second angles of the angulation are both measured in degrees relative to an upright normal position of the object, and the first and second angles of the angulation are defined in two respective vertical planes that are perpendicular to each other.

17. A device for indicating an angulation of an object in an x-ray image, the device comprising:
an enclosure being configured so as to be attached to a front surface of a cassette used for x-ray imaging, the enclosure having a first passageway within the enclosure through which a first radiopaque movable object travels in relation to a first angle at which the cassette is disposed, and the enclosure having a second passageway within the enclosure through which a second radiopaque movable object travels in relation to a second angle at which the cassette is disposed, wherein the first and second passageways are both arcuate, the first arcuate passageway is disposed in a first plane, the second arcuate passageway is disposed in a second plane, and the first and second planes are perpendicular to each other; and
a first plurality of radiopaque markers positioned adjacent to the first passageway, and a second plurality of radiopaque markers positioned adjacent to the second passageway;
wherein a current position of the first radiopaque movable object; in relation to the first plurality of radiopaque markers represents the first angle at which the cassette is disposed, and a current position of the second radiopaque movable object in relation to the second plurality of radiopaque markers represents the second angle at which the cassette is disposed.

18. The device of claim 17, wherein the first passageway is a measurably defined passageway and is formed so as to allow the first movable object to move freely in a vertical direction.

19. The device of claim 18, wherein the second movable object is allowed to freely move from side-to-side in the second passageway in relation to a horizontal angulation of the cassette, wherein the position of the second movable object in the second passageway identifies a horizontal angulation of the cassette.

20. The device of claim 17, wherein the first movable object and the second movable object are balls.

21. An apparatus for displaying an angulation on an x-ray image, the apparatus comprising:
an x-ray device configured to produce x-ray images of an object between the x-ray device and a cassette;
a first passageway that is coupled to the cassette, wherein a first movable object travels in the first passageway in relation to an angulation at which the cassette is currently disposed;
a second passageway that is coupled to the cassette, wherein a second movable object travels in the second passageway in relation to the angulation at which the cassette is currently disposed;
a first plurality of markers positioned adjacent to the first passageway, wherein a position of the first movable object in relation to the first plurality of markers represents a first angle at which the object is positioned at a time when the x-ray image is taken; and
a second plurality of markers positioned adjacent to the second passageway, wherein a position of the second movable object in relation to the second plurality of markers represents a second angle at which the object is positioned at a time when the x-ray image is taken;
wherein the first and second angles are defined in respective perpendicular planes; and
wherein the first and second movable objects and the first and second pluralities of markers are visible on the x-ray image produced by the x-ray device.

* * * * *